United States Patent [19]

Taub

[11] Patent Number: 4,873,187

[45] Date of Patent: Oct. 10, 1989

[54] BIFUNCTIONAL DNA-PROTEIN CONJUGATING AGENT

[75] Inventor: Floyd Taub, Rockville, Md.

[73] Assignee: Digene Diagnostics, Incorporated, Silver Spring, Md.

[21] Appl. No.: 839,074

[22] Filed: Mar. 13, 1986

[51] Int. Cl.$^4$ .................. C12Q 1/68; C12Q 1/70; C12Q 1/54; C12N 9/96

[52] U.S. Cl. ................................ 435/5; 435/6; 435/14; 435/25; 435/188; 435/803; 935/78

[58] Field of Search .............. 435/6, 188, 803, 5, 435/14, 25; 935/78; 436/501; 252/547

[56] References Cited

U.S. PATENT DOCUMENTS 4,055,469 10/1977 Snoke et al. ............... 435/183
4,235,759 11/1980 Ohbu et al. .............. 252/DIG. 14 X
4,454,060 6/1984 Lai et al. .

FOREIGN PATENT DOCUMENTS

84/03717 9/1984 World Int. Prop. O. .

OTHER PUBLICATIONS

Geck, P. et al., Anal. Biochem., 135 (1983), p. 264–268.
Chem. Abst. 92, No. 1, Issued Jan. 7, 1980, p. 279, 2787k, Khristova, M. L. et al., "Use of the Cationic Detergent . . . RNA".
Renz, M. et al., Nuckic Acids Research, 12 (1984), pp. 3435–3444.

Primary Examiner—Johnnie R. Brown
Assistant Examiner—Jeremy M. Jay
Attorney, Agent, or Firm—Saidman, Sterne, Kessler & Goldstein

[57] ABSTRACT

A cationic detergent having a positively charged group and a hydrophobic group is used to conjugate an enzymatically active enzyme molecule with a single-stranded nucleic acid molecule. The conjugate may be used to detect the presence of nucleic acid molecules having a nucleotide sequence which is complementary to that of the single-stranded molecule of the conjugate.

23 Claims, No Drawings

BIFUNCTIONAL DNA-PROTEIN CONJUGATING AGENT

BACKGROUND OF THE INVENTION

Nucleic acid probes have a promising future as aids to the diagnosis of infectious and genetic diseases. In order to detect hybridization of the probe to the sample nucleic acid, one may "label" the probe. While radiolabeling is common, the probe may be non-radioisotopically labeled with a ligand, fluorescer, chemiluminescer, enzyme, or antibody. Falkow, U.S. Pat. No. 4,358,535. Use of a nonradioactive label is preferable because of the health hazards, expense and limited half life of radioisotopes.

The term "conjugating agent" is used here to refer to an agent which directly or indirectly, covalently or noncovalently, and reversibly or irreversibly, achieves a binding or association between two chemical species, such as a proteinaceous label and a nucleic acid.

A large number of covalent conjugating agents (crosslinking agents) are known in the immunoassay art, where they are used to label ligands and antibodies. (The same agents are also often used to attach immunogens to carriers.) See, for example, Halmann, U.S. Pat. No. 4,302,534, at column 2, lines 27-57; Parikh, U.S. Pat. No. 4,298,685, column 3, lines 6, 56; Singh U.S. Pat. No. 4,241,177; Rubenstein, U.S. Pat. No. 3,817,837; Farina, U.S. Pat. No. 4,378,428, column 26, line 59 through column 27, line 29; Devlin, U.S. Pat. No. 3,951,748, column 4, line 45 through column 5, line 19; and Albarella, U.S. Pat. No. 4,469,797.

A number of methods are known for covalently crosslinking proteins to nucleic acids. See EP Appl 151,001. Borel, et al., J. Immunol Methods, 67: 289-302 (1984) expressed a strong preference for glutaraldehyde as a crosslinking agent. They used it to bind an oligonucleotide to a protein carrier. Renz, EMBO J., 2: 817 (1983), used the well known cross linker glutaraldehyde to attach histones to nucleic acids. Renz also used benzoquinone to attach a uniformly positively charged polymer to a protein, thus modifying the charge on that protein so it would have sufficient affinity for nucleic acid to be crosslinked by glutaraldehyde.

This method required (1) use of unstable and toxic reagents (benzoquinone) to modify the protein; (2) separation of activated complex from free benzoquinone; (3) attachment of polymer to the activated proteins; and (4) separation of protein-bound polymer from free polymer before conjugation to nucleic acid. In practice, these steps are time consuming and may be difficult to execute properly.

This invention concerns the use of molecules, particularly charged molecules, having positive regions to bind nucleic acids and hydrophobic regions to bind proteins to modify the charge on a protein such that the protein binds the nucleic acid sufficiently to be conjugated in a single step.

It is already known in the art that a wide variety of cationic detergents, possessing hydrophobic groups on one end and positively charged groups on the other, may be prepared. See, e.g., Ohbu, U.S. Pat. No. 4,235,759; Lar, U.S. Pat. No. 4,454,060. The art fails, however, to teach that these detergents may have any value in the conjugation of nucleic acids with proteins. Indeed, cleanser compositions have been devised which are intended to break natural crosslinks in proteins. Schafer-Burkhara, U.S. Pat. No. 4,311,618.

Detergents have been utilized in the immunoassay art, but not in the manner addressed by the present invention. Albert, U.S. Pat. No. 4,486,534 teaches the isolation of immunologically active conjugates from a mixture of active and inactive conjugates by putting the mixture in contact with a carrier-bound complex-former such as a fatty acid, and eluting the inactive conjugates with a detergent. Caldwell, U.S. Pat. No. 4,427,782 teaches the use of an anionic detergent to solubilize an antigen for later purification, and use in the isolation and purification of a corresponding antibody.

Weltman, U.S. Pat. No. 4,002,532 describe use of organic polyamine conditioners in connection with the coupling of enzymes to antibodies. There is no teaching that these conditioners have any value in coupling enzymes to nucleic acids. In any event, the recited polyamines were not cationic detergents.

SUMMARY OF THE INVENTION

I have discovered that a cationic detergent may be used to conjugate a nucleic acid with a protein. A cationic detergent comprises a hydrophobic moiety, which would have affinity for the protein, and a positively charged moiety, which could interact electrostatically with the negatively charged nucleic acid. Further, other bifunctional chemicals having both hydrophobic and positively charged moieties could be used to conjugate a nucleic acid with a protein.

The hydrophobic groups which may be employed in the bifunctional reagents of the present invention include alkyl, aryl, and arylalkyl groups. The criterion is that the group be capable of interacting with the hydrophobic functionalities of a protein.

The cationic groups which may be employed in the bifunctional reagents of the present invention include primary, secondary, tertiary and quaternary amines. Thus, the group need not bear a full positive charge, but rather need have only sufficient cationic properties to render it capable of electrostatic interaction with a nucleic acid, which is negatively charged. However, use of charged molecules is preferred.

The conjugating agent of the present invention may be used to label a nucleic acid, for use in a DNA hybridization assay, with an enzyme, such as glucose oxidase.

Although the detergent may be used as the sole conjugating agent, it is preferably used to facilitate the irreversible binding of the protein to the nucleic acid by means of a crosslinking agent, such as glutaraldehyde.

The order of conjugation is irrelevant. The detergent may be conjugated first with either the nucleic acid, or the protein, or with both simultaneously.

The detergent is preferably a quaternary amine, such as dimethyl dicocoammonium chloride.

DETAILED DESCRIPTION OF THE INVENTION

By way of illustration of the utility of a detergent as a conjugating agent, the effect of a detergent and of glutaraldehyde on the conjugation of poly-A RNA and glucose oxidase was studied.

Polyribonucleotide A (poly A) has been successfully crosslinked with glucose oxidase using various concentrations of detergent #1 (Arguad $^{(R)}$2C-75, loc 1401004, supplied by AKZO chemical company; which is 75% active dimethyldicoco ammonium chloride) and glutaraldehyde. Poly A was used in these experiments as a nucleic acid system due to the ease of separation of the conjugated from free glucose oxidase using an Oligo-dT cellulose column.

Conjugation reactions were made by adding 100 ug poly A (Sigma) in 44 ul, 200 ug glucose oxidase (Sigma) in 2 ul, and varying amounts of a 1% detergent solution to make final concentrations of 0%, 0.02%, 0.05%, 0.1%, 0.15% and 0.2%. The ratio of glucose oxidase to poly A was maintained at 2:1 and glutaraldehyde was added to a final concentration of 1.0%.

Glucose Oxidase conjugated to poly A was separated from free glucose oxidase by loading 50 ug of conjugated poly A onto a column consisting of 0.25 grams of oligo-dT cellulose (Collaborative Research). The sample was absorbed into the resin bed and was washed to remove free enzyme with approximately 10.5 ml of loading buffer 20 mM sodium citrate, pH 7.2; 0.4M Nacl). Eight fractions of approximately 1.3 ml each were collected. The poly A-glucose oxidase conjugate hybridized to the oligo-dT cellulose and was eluted from the column by washing with 20 mM sodium citrate pH 7.2. Fractions were collected (as described above) and 100 ul of each fraction was sampled for measurement of glucose oxidase activity by reaction with 100 ul of glucose oxidase reagent. This reagent consists of 1.6 mg/ml orthophenylenediamine (OPD), 3.3% B-D-/glucose, 60 ug horseradish peroxidase, 50 mM NaOAc, pH 5.1.

Following conjugation with glucose oxidase, two peaks are eluted from the column. One is in the wash fractions (free glucose oxidase) and the other is in the elution fractions (poly A-glucose oxidase conjugate).

The results of the poly A-glucose oxidase conjugation show that conjugation occurs when 0.1%–0.2% detergent are included in the conjugation reaction. However, at detergent concentrations of 0.15% and 0.2% a precipitate forms which contains unknown amounts of poly A and possibly glucose oxidase as well. No conjugation was seen with detergent concentrations of 0% or 0.02% and very little (if any) conjugation occurred with a detergent concentration of 0.05%. Quantitation of the amount of glucose oxidase present in the poly A bound to the oligo-dT is presented in Table 1. For a conjugation containing 0% detergent the mass ratio of glucose oxidase to poly A could not be calculated since no glucose oxidase was detected. The ratio was 0.24 for a conjugation containing 0.1% detergent. This ratio was also unavailable for the conjugation containing 0.2% as most of the poly A precipitated out of the solution.

Results of the experiments show that the 0.1% detergent is optimal for conjugation of poly A to glucose oxidase under the conditions used.

Use of percipitating amounts of detergent may be useful in concentrating dilute solutions of DNA.

TABLE 1

Amount of Glucose Oxidase Conjugated to Poly A with Various Concentrations of Detergent

| Concentration of Detergent | $OD_{450}$[1] | Glucose Oxidase ng/100 ul[2] | Poly A ng/100 ul[3] | Ratio of Glucose Oxidase to Poly A |
|---|---|---|---|---|
| 0 | 0.010 | below assay limits[4] | not tested | — |
| .1 | 0.389 | 12 | 500 | 0.24 |

TABLE 1-continued

Amount of Glucose Oxidase Conjugated to Poly A with Various Concentrations of Detergent

| Concentration of Detergent | $OD_{450}$[1] | Glucose Oxidase ng/100 ul[2] | Poly A ng/100 ul[3] | Ratio of Glucose Oxidase to Poly A |
|---|---|---|---|---|
| .2 | 0.064 | 2 | none detected | — |

[1]Absorbance of OPD assay for gluccose oxidase activity.
[2]As calculated from 1 by standard curve.
[3]As measured by $OD_{260}$.
[4]Less than 0.5 ng.

I claim:
1. A method of detecting nucleic acid hybridization which comprises:
   A. incubating (i) a sample suspected of containing a nucleic acid molecule (I) whose presence is sought to be detected with (ii) a conjugate of a single-stranded nucleic acid molecule (II) and an enzyme molecule, said conjugate comprising the following components: (a) said single-stranded nucleic acid molecule (II), (b) said enzyme molecule, and (c) a cationic detergent, wherein said cationic detergent has a positively charged group and a hydrophobic group; and wherein said enzyme of said conjugate is enzymatically active and wherein said single-stranded nucleic acid molecule (II) is complementary to said nucleic acid molecule (I); and
   B. detecting said nucleic acid hybridization by detecting any enzyme molecule of said conjugate (ii) wherein the single-stranded nucleic acid molecule (II) of said conjugate has hybridized with said nucleic acid molecule (I).
2. The method of claim 1, wherein said conjugate is present at a concentration of at least about 1.0 g/ml.
3. The method of claim 1, wherein said nucleic acid molecule (I) is DNA.
4. The method of claim 3, wherein said nucleic acid molecule (I) is bound to a solid support.
5. The method of claim 1, wherein said nucleic acid molecule (I) is selected from the group consisting of: a viral nucleic acid molecule; a prokaryotic nucleic acid molecule; and a eukaryotic nucleic acid molecule.
6. The method of claim 5, wherein said nucleic acid molecule (I) is a bacterial prokaryotic nucleic acid molecule.
7. The method of claim 5, wherein said nucleic acid molecule (I) is a mammalian eukaryotic nucleic acid molecule.
8. The method of claim 5, wherein said nucleic acid molecule (I) is a viral nucleic acid molecule.
9. In the formation of a conjugate of an enzyme and a nucleic acid molecule, the improvement comprising using a detergent to form said conjugate, wherein said detergent is a cationic detergent having a positively charged group and a hydrophobic group, and wherein said enzyme is enzymatically active.
10. A conjugate of a single-stranded nucleic acid molecule and an enzymatically active enzyme molecule, said conjugate comprising the following components:
   (a) said nucleic acid molecule;
   (b) said enzyme molecule; and
   (c) a cationic detergent;
wherein said cationic detergent has a positively charged group and a hydrophobic group; and wherein said enzyme of said conjugate is enzymatically active.

11. The conjugate of claim 10, which additionally contains a covalent crosslinking agent capable of covalently crosslinking said enzyme to said nucleic acid.

12. The conjugate of claim 11, wherein said covalent crosslinking agent is glutaraldehyde.

13. The conjugate of claim 10, wherein said detergent is dimethyl dicocoammonium chloride.

14. The conjugate of claim 13, which additionally contains a covalent cross-linking agent capable of covalently cross-linking said enzyme to said nucleic acid.

15. The conjugate of claim 14, wherein said covalent cross-linking agent is glutaraldehyde.

16. A method of conjugating a nucleic acid molecule with an enzymatically active enzyme molecule to form a conjugate of said nucleic acid molecule and said enzyme, wherein said enzyme of said conjugate is enzymatically active, said method comprising coupling a cationic detergent having a positively charged group and a hydrophobic group with said nucleic acid molecule and said enzyme.

17. The method of claim 16, wherein said cationic detergent is coupled with said nucleic acid molecule prior to coupling with said enzyme molecule.

18. The method of claim 16, wherein said cationic detergent is coupled with said enzyme molecule prior to coupling with said nucleic acid molecule.

19. The method of claim 16, wherein said cationic detergent is coupled with said nucleic acid molecule said enzyme molecule simultaneously.

20. The method of claim 16, wherein said cationic detergent contains quaternary amine.

21. The method of claim 16, wherein said enzyme molecule is glucose oxidase.

22. The method of claim 16, wherein said detergent is provided at a concentration of about 0.1 to about 0.2%.

23. The method of claim 16, wherein said detergent is a dimethyl dicocoammonium salt.

* * * * *